United States Patent [19]
Konno et al.

[11] 4,268,501
[45] May 19, 1981

[54] SUPPOSITORIES CONTAINING A COMPOUND HAVING BRONCHODILATOR ACTIVITY

[75] Inventors: Yutaka Konno, Omiya; Shigeo Kawamura, Urawa, both of Japan

[73] Assignee: Yamanouchi Pharmaceutical Co., Ltd., Tokyo, Japan

[21] Appl. No.: 101,012

[22] Filed: Dec. 5, 1979

[30] Foreign Application Priority Data

Dec. 29, 1978 [JP] Japan .................. 53-165426

[51] Int. Cl.³ .................. A61K 31/79; A61K 31/225
[52] U.S. Cl. .................. 424/80; 424/313; 424/330; 424/DIG. 15
[58] Field of Search .......... 424/80, 313, 330, DIG. 15

[56] References Cited

U.S. PATENT DOCUMENTS

| | | | |
|---|---|---|---|
| 3,234,091 | 2/1966 | Lang et al. | 424/DIG. 15 X |
| 3,262,849 | 7/1966 | Lietz et al. | 424/DIG. 15 X |
| 3,994,974 | 11/1976 | Murakami | 260/562 A |

OTHER PUBLICATIONS

Foye "Principles of Medicinal Chemistry", pp. 802-804, (1976).
Chemical Abstracts, 85:99180y, (1976).

*Primary Examiner*—Leonard Schenkman
*Attorney, Agent, or Firm*—Burgess, Ryan and Wayne

[57] ABSTRACT

A stable suppository useful as an antiasthmatic agent containing 3-formylamino-4-hydroxy-α-[N-(1-methyl-2-p-methoxyphenylethyl)aminomethyl]benzyl alcohol-½fumarate monohydrate, polyvinyl pyrrolidone, and at least one of cyclodextrin, dextran and magnesium metasilicate aluminate together with a suppository base.

7 Claims, No Drawings

SUPPOSITORIES CONTAINING A COMPOUND HAVING BRONCHODILATOR ACTIVITY

BACKGROUND OF THE INVENTION

1. Field of the Invention:

This invention relates to a stable suppository containing 3-formylamino-4-hydroxy-$\alpha$-[N-(1-methyl-2-p-methoxyphenylethyl)aminomethyl]benzyl alcohol-½fumarate mono-hydrate (hereinafter, referred to as BD-40A).

2. Description of the Prior Art:

BD-40A possesses a strong and prolonged bronchodilator activity and is very useful as an antiasthmatic agent (see, U.S. Pat. No. 3,994,974). In general, when a patient has an asthmatic spasm, it is sometimes very difficult to orally administer medicaments and even if the patient can take a medicament, it sometimes happens that the patient disgorges the medicament by coughing and hence the desired purpose cannot be attained. Also, an asthmatic patient has a tendency of being afflicted with a spasm at night and for prophylaxis, a medicament is sometimes administered before sleeping or, in case of infants, etc., after sleeping. Therefore, the development of suppositories containing BD-40A which can be parenterally administered had been desired.

However, BD-40A is unexpectedly unstable in the form of a suppository although BD-40A itself is chemically stable. Decomposition of BD-40A occurs when the compound is incorporated into an ordinary suppository base such as polyethylene glycol, glycerogelatin, a glycerol triester of a higher fatty acid [This triester usually includes a small quantity of mono- and di-ester. As such substance, for example, "semi-synthetic glycerides" (Frech pharmacopoeia), "Witepsol" (registered trademark, made by Dynamit Nobel A.G.) are illustrated, and these include a small quantity of mono- and di-ester; hereinafter, the term "a glycerol triester of a higher fatty acid" is used in this meaning] as well as when it is formulated with additives such as a surface active agent, a higher fatty alcohol, etc., and hence it was generally very difficult to use BD-40A for practical purposes in the form of a suppository.

SUMMARY OF THE INVENTION

As the result of various investigations on the stabilization of BD-40A in the form of a suppository, the inventors have discovered that good results are obtained by formulating BD-40A with an ordinary suppository base, polyvinyl pyrrolidone, and at least one of cyclodextrin, dextran, and magnesium metasilicate aluminate.

That is, this invention provides a stable suppository comprising BD-40A formulated with polyvinyl pyrrolidone and at least one of cyclodextrin, dextran and magnesium metasilicate aluminate together with a suppository base.

DESCRIPTION OF THE PREFERRED EMBODIMENTS

Now, polyvinyl pyrrolidone, cyclodextrin, dextran, and magnesium metasilicate aluminate (hereinafter, they are referred to as stabilizing components) are not ones usually used as excipients for suppositories and hence it was utterly unexpected that the stabilization of BD-40A in the form of a suppository could be attained by formulating with these stabilizing components.

The mean molecular weight of polyvinyl pyrrolidone used as a stabilizing component in this invention is 10,000 to 700,000, preferably 25,000 to 160,000. As cyclodextrin, $\alpha$-, $\beta$-, and $\gamma$-cyclodextrins may be used but $\beta$-cyclodextrin is usually used. The mean molecular weight of dextran used in this invention is usually less than about 4,000,000, preferably 20,000 to 100,000. The proportions of these stabilizing components based on the weight of BD-40A are 1-200 times, preferably 10-15 times for polyvinyl pyrrolidone and 20-500 times, preferably 50-200 times for cyclodextrin, dextran and magnesium metasilicate aluminate.

The suppository of this invention is usually prepared by mixing BD-40A and the stabilizing components in a proper solvent, if necessary, with stirring under heating and then evaporating off the solvent to dry. Any solvents which can dissolve BD-40A and polyvinyl pyrrolidone may be used without particular restriction but usually, water, methanol, ethanol or other organic solvents which are easily miscible with water are used solely or as a proper mixture of them.

A solid mixture of BD-40A and stabilizing components obtained by removing the solvent is ground and mixed with a suppository base. Thereafter, a suppository is prepared by pouring the mixture into a suppository mold or filling into gelatin rectal capsules according to an ordinary procedure for preparing a suppository. In this case, as the suppository base, polyethylene glycol, glycerogelatin, or a glycerol ester of a higher fatty acid may be used but the use of a glycerol ester of a higher fatty acid is particularly preferred.

In the suppository of this invention prepared as described above, BD-40A is very stable. The BD-40A remaining (%) in the suppositories of this invention for one month in a vessel at a storage temperature of 50° C. or 60° C. is shown in the following table together with the results of control suppositories.

TABLE

| Composition | C-1 | C-2 | C-3 | E-1 | E-2 | E-3 |
|---|---|---|---|---|---|---|
| BD-40A | 0.01g | 0.01g | 0.01g | 0.01g | 0.01g | 0.01g |
| Witepsol* (base) | 100g | 100g | 100g | 100g | 100g | 100g |
| Polyvinyl pyrrolidone (mean mol. weight 40,000) | — | 0.2g | — | 0.2g | 0.2g | 0.2g |
| Dextran (mean mol weight 40,000) | — | — | 0.8g | 0.8g | — | — |
| $\beta$-Cyclodextrin | — | — | — | — | 0.8g | — |
| Magnesium metasilicate aluminate** | — | — | — | — | — | 0.8g |
| BD-40A remaining (%) | | | | | | |
| At the zero-time | 100 | 100 | 100 | 100 | 100 | 100 |
| After 1 month at 50° C. | 82.9 | 90.6 | 58.7 | 92.0 | 96.9 | 95.3 |
| After 1 month at 60° C. | 66.9 | 78.2 | 42.3 | 90.7 | 94.4 | 89.3 |

*Registered trade mark of glycerol triester of higher fatty acid, made by Dynamit Nobel A.G.
**Neusilin; registered trade mark, made by Fuji Kagaku Kogyo K. K.
C-1, C-2 and C-3/ stand for Control-1,2 and 3,/ and E-1, E-2 and E-3 stand for Example-1, 2 and 3, respectively.

In addition, the determination method of BD-40A concentration and the preparation method for the control suppositories are briefly shown below:

Determination method:

About 2 of the suppository accurately weighed is dissolved in one ml of chloroform and after adding accurately 20 ml of a 0.02 M citrate buffer solution (pH 5.0) to the solution, the mixture is heated to about 50° C. for 2 minutes and shaken for 20 minutes. Then, the mixture is subjected to centrifugal separation and an aliquot of the supernatant is determined by means of high speed liquid chromatography using a column packed with LiChrosorb RP-18 (registered trade mark, made by Merck & Co., Inc.).

Preparation of Control-1:

After melting 100 g of Witepsol, 0.01 g of BD-40A is added to the melt with stirring by means of a homogenizer. After stirring the mixture well, the mixture is poured into a suppository mold to prepare 100 suppositories.

Preparation of Control-2:

In 50 ml of ethanol are dissolved 0.1 g of BD-40A and 2 g of polyvinyl pyrrolidone. The solvent is removed by rotary-evaporation and the residue formed is dried by vacuum. The solid mixture formed is ground in a mortar and in an amount of the dried preparation corresponding to 0.01 g of BD-40A is added to 100 g of molten Witepsol with stirring by means of a homogenizer. After stirring well, the mixture is poured into a suppository mold to prepare 100 suppositories.

Preparation of Control-3:

In 5 ml of ethanol is dissolved 0.01 g of BD-40A and then 0.8 g of dextran is added to the solution. After shaking well, the solvent is removed by rotary-evaporation and the residue formed is dried by vacuum. The solid product thus obtained is ground by means of a mortar and the powder formed is added to 100 g of molten Witepsol with stirring by means of a homogenizer. After stirring well, the mixture is poured into a suppository mold to prepare 100 suppositories.

Then, the suppositories of this invention will be further explained by the following examples.

EXAMPLE 1

In 5 ml of ethanol are dissolved 0.01 g of BD-40A and 0.2 g of polyvinyl pyrrolidone and then 0.8 g of dextran is added to the solution. After shaking the mixture well, the solvent is removed by rotary-evaporation and the residue formed is dried by vacuum. The solid product thus obtained is ground by means of a mortar. The powder formed is added to 100 g of molten Witepsol with stirring by means of a homogenizer. After stirring well, the mixture is poured into a suppository mold to prepare 100 suppositories each containing 100 μg of BD-40A.

EXAMPLE 2

In 15 ml of a mixture of water and ethanol (1:1 by volume ratio) are dissolved 0.01 g of BD-40A, 0.2 g of polyvinyl pyrrolidone, and 0.8 g of β-cyclodextrin. Then, the solvent is removed by rotary-evaporation and the residue formed is dried by vacuum. The solid product thus obtained is ground by means of a mortar and the powder formed is added to 100 g of molten Witepsol with stirring by means of a homogenizer. After stirring well, the mixture is poured into a suppository mold to prepare 100 suppositories each containing 100 μg of BD-40A.

EXAMPLE 3

In 5 ml of ethanol are dissolved 0.01 g of BD-40A and 0.2 g of polyvinyl pyrrolidone and then 0.8 g of magnesium metasilicate aluminate is added to the solution. After shaking the mixture well, the solvent is removed by rotary-evaporation and the residue formed is dried by vacuum. The solid product thus obtained is ground by means of a mortar and the powder formed is added to 100 g of molten Witepsol with stirring by means of a homogenizer. After stirring well, the mixture is poured into a suppository mold to prepare 100 suppositories each containing 100 μg of BD-40A.

What is claimed is:

1. A stable suppository comprising:
   (A) an anti-asthmatic effective amount of 3-formylamino-4-hydroxy-α-benzyl alcohol.½fumarate mono-hydrate as the active ingredient, compounded with
   (B) a stabilizing effective amount of stabilizing components comprising polyvinyl pyrrolidone and at least one member selected from the group consisting of cyclodextrin, dextran and magnesium metasilicate aluminate, and
   (C) a suppository base.

2. The stable suppository as claimed in claim 1 wherein said suppository heat base is a glycerol triester of a higher fatty acid.

3. The stable suppository as claimed in claim 1 wherein said member is β-cyclodextrin and said suppository base is a glycerol triester of a higher fatty acid.

4. The stable suppository as claimed in claim 1 wherein the amount of polyvinyl pyrrolidone is 1–200 parts by weight based on the weight of the active ingredient and the amount of at least one of cyclodextrin, dextran and magnesium metasilicate aluminate is 20–500 parts by weight based on the weight of the active ingredient.

5. The stable suppository as claimed in claim 3 wherein the amount of polyvinyl pyrrolidone is 1–200 parts by weight based on the weight of the active ingredient and the amount of β-cyclodextrin is 20–500 parts by weight based on the weight of the active ingredient.

6. The stable suppository as claimed in claim 1 wherein the amount of polyvinyl pyrrolidone is 10–50 parts by weight based on the weight of the active ingredient and the amount of at least one of cyclodextrin, dextran and magnesium metasilicate aluminate is 50–200 parts by weight based on the weight of the active ingredient.

7. The stable suppository as claimed in claim 3 wherein the amount of polyvinyl pyrrolidone is 10–50 parts by weight based on the weight of the active ingredient and the amount of β-cyclodextrin is 50–200 parts by weight based on the weight of the active ingredient.

\* \* \* \* \*